(12) United States Patent
Gardner et al.

(10) Patent No.: US 7,981,035 B2
(45) Date of Patent: Jul. 19, 2011

(54) PHASE SELECTION FOR CARDIAC CONTRAST ASSESSMENT

(75) Inventors: Edward A. Gardner, San Jose, CA (US); Michael N. Woelmer, Milan, MI (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 334 days.

(21) Appl. No.: 11/904,662

(22) Filed: Sep. 27, 2007

(65) Prior Publication Data
US 2008/0033294 A1 Feb. 7, 2008

Related U.S. Application Data

(62) Division of application No. 10/778,665, filed on Feb. 13, 2004, now Pat. No. 7,731,660.

(60) Provisional application No. 60/490,324, filed on Jul. 25, 2003.

(51) Int. Cl.
*A61B 8/00* (2006.01)
(52) U.S. Cl. ......... 600/437; 600/407; 600/458; 382/128
(58) Field of Classification Search .................. 382/128; 600/407, 437, 458
See application file for complete search history.

(56) References Cited

U.S. PATENT DOCUMENTS

| | | |
|---|---|---|
| 4,373,533 A | 2/1983 | Iinuma |
| 5,355,887 A | 10/1994 | Iizuka et al. |
| 5,456,255 A | 10/1995 | Abe et al. |
| 5,538,003 A | 7/1996 | Gadonniex et al. |
| 5,615,680 A | 4/1997 | Sano |
| 5,657,760 A | 8/1997 | Ying et al. |
| 5,701,897 A | 12/1997 | Sano |
| 5,743,266 A | 4/1998 | Levene et al. |
| 5,785,654 A | 7/1998 | Iinuma et al. |
| 5,820,561 A | 10/1998 | Olstad et al. |
| 6,030,344 A | 2/2000 | Guracar et al. |
| 6,174,287 B1 | 1/2001 | Resnick et al. |
| 6,193,660 B1 | 2/2001 | Jackson et al. |
| 6,213,945 B1 | 4/2001 | Tynan |
| 6,217,520 B1 | 4/2001 | He et al. |
| 6,306,095 B1 | 10/2001 | Holley et al. |
| 6,346,124 B1 | 2/2002 | Geiser et al. |
| 6,352,507 B1 | 3/2002 | Torp et al. |
| 6,360,027 B1 | 3/2002 | Hossack et al. |
| 6,447,453 B1 | 9/2002 | Roudhill et al. |

(Continued)

OTHER PUBLICATIONS

Cwajg et al. "Detection of Angiographically Significant Coronary Artery Disease with Accelerated Intermittent Imaging and Intravenous Administration of Ultrasound Contrast Materials," American Heart J. 139: 675-683 (2000).

(Continued)

*Primary Examiner* — Tse Chen
*Assistant Examiner* — Peter Luong (57) ABSTRACT

In one embodiment, at least one visual characteristic from a selected image is used to automatically select an ultrasound image from a set of images from a plurality of heart cycles. In another embodiment, motion correction is performed on ultrasound images that are automatically selected from a plurality of ultrasound images associated with the same phase of the heart cycle. In yet another embodiment, ultrasound images are automatically selected from a set of images based on a time interval that is within a tolerance range from a reference phase of the heart cycle. In another embodiment, a stored user-preference of a phase of the heart cycle is used to automatically select an ultrasound image from a set of images. In yet another embodiment, a user-defined region of interest is placed on an ultrasound image associated with a selected phase of a heart cycle.

26 Claims, 4 Drawing Sheets

U.S. PATENT DOCUMENTS

| | | |
|---|---|---|
| 6,458,082 B1 | 10/2002 | Jackson et al. |
| 6,491,636 B2 | 12/2002 | Chenal et al. |
| 6,500,121 B1 | 12/2002 | Slayton et al. |
| 6,558,325 B1 | 5/2003 | Pang et al. |
| 6,579,240 B2 | 6/2003 | Bjaerum et al. |
| 6,673,017 B1 | 1/2004 | Jackson |
| 6,692,438 B2 | 2/2004 | Skyba et al. |
| 6,884,216 B2 | 4/2005 | Abe et al. |
| 6,980,844 B2 | 12/2005 | Schoisswhl |
| 6,994,673 B2 | 2/2006 | Lysyansky et al. |
| 2003/0114759 A1 | 6/2003 | Skyba et al. |
| 2004/0064036 A1 | 4/2004 | Mao et al. |
| 2004/0066389 A1 | 4/2004 | Skyba et al. |
| 2004/0066957 A1 | 4/2004 | Miller et al. |
| 2005/0033123 A1 | 2/2005 | Gardner et al. |
| 2005/0033179 A1 | 2/2005 | Gardner et al. |
| 2008/0027319 A1 | 1/2008 | Gardner et al. |
| 2009/0010511 A1 | 1/2009 | Gardner et al. |
| 2009/0016586 A1 | 1/2009 | Gardner et al. |

OTHER PUBLICATIONS

Wei et al. "Basis for Detection of Stenosis Using Venous Administration of Microbubbles During Myocardial Contrast Echocardiography: Bolus or Continuous Infusion," JACC 32: 252-60 (Jul. 1998).

Wel et al., "Noninvasive Quantification of Coronary Blood Flow Reserve in Humans Using Myocardial Contrast Echocardiography," Circulation 103: 2560-2565 (2001).

Skyba et al., "Methods for Quantitative Analysis," Chapter 4, Handbook of Contrast Echocardiography, pp. 154-171 (Jun. 2000).

"QLAB—Region of Interest (ROI) Quantification," http://www.medical.philips.com/main/products/ultrasound/general/glab/features/roi/, 1 page (printed 2003).

"QLAB Advanced Quantification for Ultrasound," http://www.medical.philips.com/main/products/ultrasound/assets/docs/cardiology/glab_spec_sheet.pdf, 2 pages (2002).

PHASE SELECTION FOR CARDIAC CONTRAST ASSESSMENT

CROSS-REFERENCE TO RELATED APPLICATION

This application is a divisional of U.S. patent application Ser. No. 10/778,665, filed Feb. 13, 2004, now U.S. Pat. No. 7,731,660.

RELATED APPLICATION

This application claims the benefit of U.S. Provisional Application No. 60/490,324, filed Jul. 25, 2003, which is hereby incorporated by reference herein.

BACKGROUND

Contrast agents can be used in a medical ultrasound examination to enhance diagnosis. The rate of contrast agent enhancement of tissue relates to the rate of blood flow to the tissue and can be used to diagnose a variety of disease states. While contrast agent quantification can be performed over an entire heart cycle, techniques have been discussed for performing quantification on specific parts of the heart cycle. For example, U.S. Patent Application Publication No. US2003/0114759A1 to Skyba et al. describes an ultrasonic imaging system and method for displaying tissue perfusion and other parameters varying with time in which gated or ungated images are used to enable a parametric display to be keyed to specific phases of the heart cycle. Additionally, QLAB Software by Philips Medical Systems has been described as containing custom tools to "auto trim" relative to an ECG trigger for quantification of specific parts of a cardiac cycle.

SUMMARY

The present invention is defined by the following claims, and nothing in this section should be taken as a limitation on those claims.

By way of introduction, the embodiments described below relate to phase selection for cardiac contrast assessment. In one embodiment, at least one visual characteristic from a selected image is used to automatically select an ultrasound image from a set of images from a plurality of heart cycles. In another embodiment, motion correction is performed on ultrasound images that are automatically selected from a plurality of ultrasound images associated with the same phase of the heart cycle. In yet another embodiment, ultrasound images are automatically selected from a set of images based on a time interval that is within a tolerance range from a reference phase of the heart cycle. In another embodiment, a stored user-preference of a phase of the heart cycle is used to automatically select an ultrasound image from a set of images. In yet another embodiment, a user-defined region of interest is placed on an ultrasound image associated with a selected phase of a heart cycle. Other embodiments are provided, and each of the embodiments described herein can be used alone or in combination with one another.

The embodiments will now be described with reference to the attached drawings.

DETAILED DESCRIPTION OF THE PRESENTLY PREFERRED EMBODIMENTS

Introduction

Figure 1:
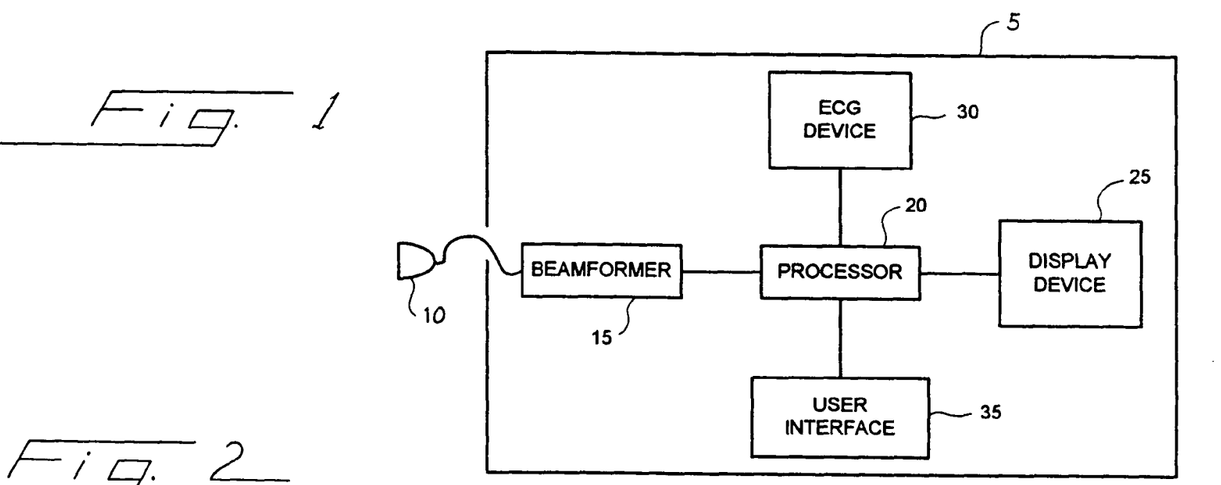
FIG. 1 is a block diagram of a medical diagnostic ultrasound imaging system of an embodiment.

Turning to the drawings, FIG. 1 is a block diagram of a medical diagnostic ultrasound imaging system 100 that can be used with the embodiments described herein, which generally relate to diagnostic ultrasonic imaging with contrast agents. As shown in FIG. 1, the ultrasound system 5 comprises a transducer probe 10, a beamformer 15, a processor 20, a display device 25, an ECG device 30, and a user interface 35, each of which is in communication with the other through one or more named or unnamed components. Two components can be in communication with each other through a wired or wireless connection. The term "processor" broadly refers to the appropriate hardware and/or software components of the ultrasound system 5 that can be used to implement the functionality described herein. The ultrasound system 5 can comprise additional components, which are not shown in FIG. 1 for simplicity.

During an ultrasound examination, a sonographer contacts the transducer probe 10 with a patient, and the ultrasound system's processor 20 causes the beamformer 15 to apply a voltage to the transducer 10 to cause it to vibrate and emit an ultrasonic beam into the portion of the patient's body in contact with the transducer 10. Ultrasonic energy reflected from the patient's body impinges on the transducer 10, and the resulting voltages created by the transducer 10 are received by the beamformer 15. The processor 20 processes the sensed voltages to create an ultrasound image and displays the image on the display device 25. The ECG device 30 captures ECG information (e.g., a heart cycle waveform) from the patient. The ECG information can be displayed with an ultrasound image during image acquisition. Additionally, the ECG information can be stored with an ultrasound image on a storage device internal or external to the ultrasound system 5 for later review.

The ultrasound system 5 can be used for contrast agent imaging to enhance diagnosis. Venous injection of contrast agent causes an increase in the ultrasound signal when the contrast agent washes into the tissue being imaged. In operation, a high-intensity ultrasound pulse is transmitted to destroy contrast agent in a tissue, and then the high-intensity ultrasound pulse is turned off and the tissue is imaged as new contrast-agent-filled blood perfuses into the tissue. The rate of the contrast agent enhancement (or "wash-in") relates to the rate of blood flow to the tissue and ultimately to tissue perfusion. Because of this, the time course of contrast enhancement can be assessed to diagnose a variety of disease states from coronary artery disease to tumor neovasculature to liver metastases. As used herein, the phrase "assessment of the time course of contrast enhancement" refers to either qualitative or quantitative assessment of contrast ultrasound images. All of these techniques rely on comparisons between images acquired at different times in order to see the variation caused by contrast agent enhancement. These techniques will now be discussed.

Qualitative assessment is the simplest method of determining the time course of contrast enhancement and relies on observing, by eye, the visible changes in an ultrasound image caused by contrast agent. Qualitative assessment had been done successfully for coronary perfusion assessment (Cwajg et al., "Detection of Angiographically Significant Coronary Artery Disease with Accelerated Intermittent Imaging and Intravenous Administration of Ultrasound Contrast Materials," American Heart J. 139: 675-683 (2000)) and characterization of liver diseases. Diagnoses can be made by simply observing the contrast enhancement in a "live" ultrasound image or by reviewing a stored image clip.

Quantitative assessment (or analysis) refers to time intensity curve analysis, parametric imaging, displaying results of calculations, or any other contrast enhancement assessment technique (now existing or later developed) other than pure qualitative analysis. Time intensity curve (TIC) analysis allows more precise assessment of the time course of contrast enhancement than can be made by eye alone. TIC's present the variation of the average signal level or number of color pixels in a number of regions of interest (ROI's) in graphical form to identify contrast enhancement differences between the regions. The data is also fit to functional curves, the parameters of which are used to make absolute determinations of flow characteristics (Wei et al., "Basis for Detection of Stenosis Using Venous Administration of Microbubbles During Myocardial Contrast Echocardiography: Bolus or Continuous Infusion," JACC 32: 252-60 (July 1998)). These parameters can be related to coronary flow reserve (Wei et al., "Noninvasive Quantification of Coronary Blood Flow Reserve in Humans Using Myocardial Contrast Echocardiography," Circulation 103: 2560-2565 (2001)) and can be used to make diagnoses.

Figure 2:
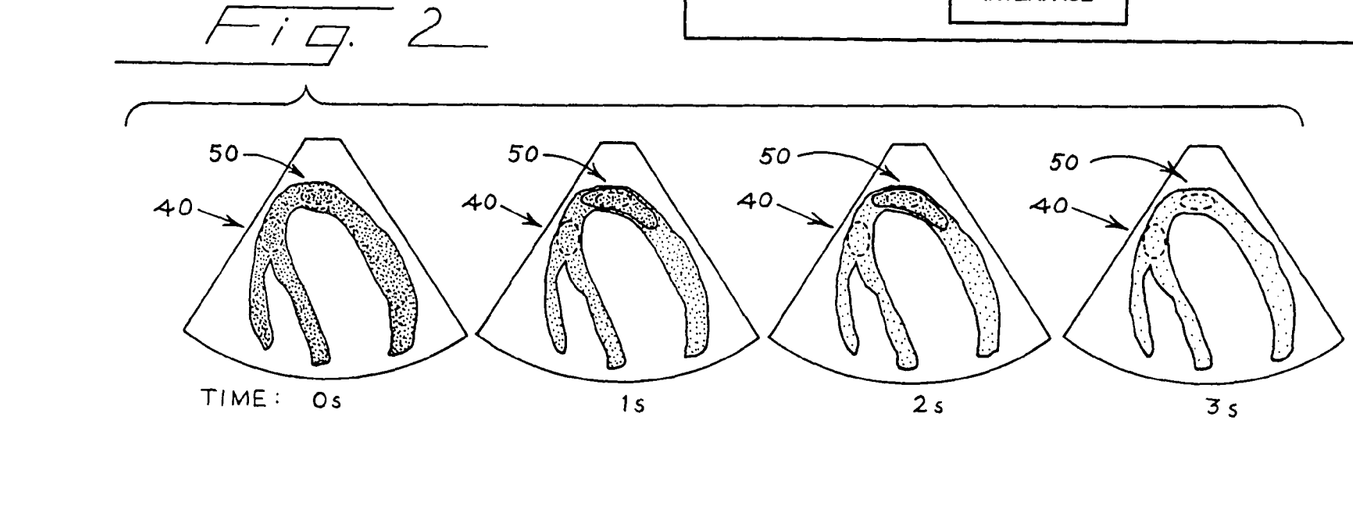
FIG. 2 is a schematic of ultrasound images showing the time course of contrast agent into a heart.
Figure 3:
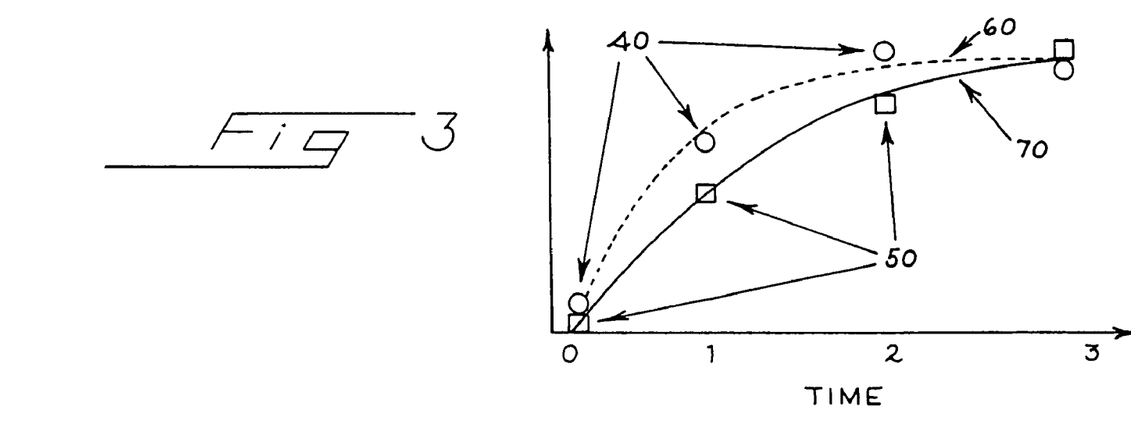
FIG. 3 shows time intensity curves of an embodiment.

FIGS. 2 and 3 illustrate the use of TICs. FIG. 2 is a schematic of ultrasound images showing the time course of contrast agent into a heart. The image at time 0 seconds was taken before the start of contrast agent wash-in, and the images at times 1 second, 2 seconds, and 3 seconds were taken during contrast wash-in. As shown in these images, the signal from tissue grows over time, but enhancement is slower in the top part of the image, indicating a problem in blood flow. Quantification is accomplished by placing two regions of interest 40, 50 at different regions of the heart image. Changes in the pixel intensity in the two regions of interest 40, 50 is indicative of contrast wash-in in those regions 40, 50, and the average intensity from within those regions 40, 50 is plotted in time-intensity curves (see FIG. 3). The time-intensity curves show that the contrast enhancement in region of interest 50 is slower than the contrast enhancement in region of interest 40 by virtue of the reduced signal at times 1 second and 2 seconds. The data points in the time intensity curves are fitted with smooth functions 60, 70, and parameters of these functions are related to the blood flow in the tissue.

TIC analysis has had limited penetration into the market due to the relatively time-consuming analysis required and the lack of spatial information derived from a small number of ROI's. Removing this obstacle while maintaining much of its sensitivity is parametric imaging. Parametric imaging combines the spatial resolution and ease of use of qualitative assessment with the sensitivity of quantitative curve fitting. In parametric imaging, the variation over time of signal level from each pixel is fitted by some function that relates to a physiological phenomenon. Selected parameters from the function for each pixel can then be combined into an image to show variation in the entire series in a static image. For contrast agent imaging, some parameter or combination of parameters related to contrast wash-in is displayed in this parametric image. In this way, spatial variation of the wash-in time course can be easily assessed.

Motion Effects on the Assessment of the Time Course of Contrast Enhancement

During a myocardial contrast imaging exam, cardiac ultrasound images are acquired at a high frame rate (typically, more than 15 frames per second) in order to provide wall motion information for qualitative wall motion assessment as well as to facilitate maintaining the scan plane. However, this high frame rate provides little additional information for quantification assessment, and cardiac motion shown by this high frame rate can make quantification difficult. For example, cardiac motion can cause substantial changes in intensity from different regions. These cyclic changes are apparent in time intensity curves generated from each frame in a real-time clip. It is also difficult or impossible to maintain the same tissue in a ROI through the cardiac cycle. Thickening causes the tissue in a fixed area to change, and any rotation of the heart will also cause different tissue to be in the image plane at different phases of the heart cycle.

One solution to this problem is to select one image from each heart cycle for analysis. (As described below, in some situations, more than one image from each heart cycle can be selected.) The selection of images from the same phase of the heart cycle prevents contractile cardiac motion from interfering with quantification of myocardial perfusion because subsequent analysis (preferably including ROI placement) is based on the set of images acquired at the selected phase instead of all of the acquired images. (As used herein, "set" refers to a group of one or more than one member.)

Figure 4:
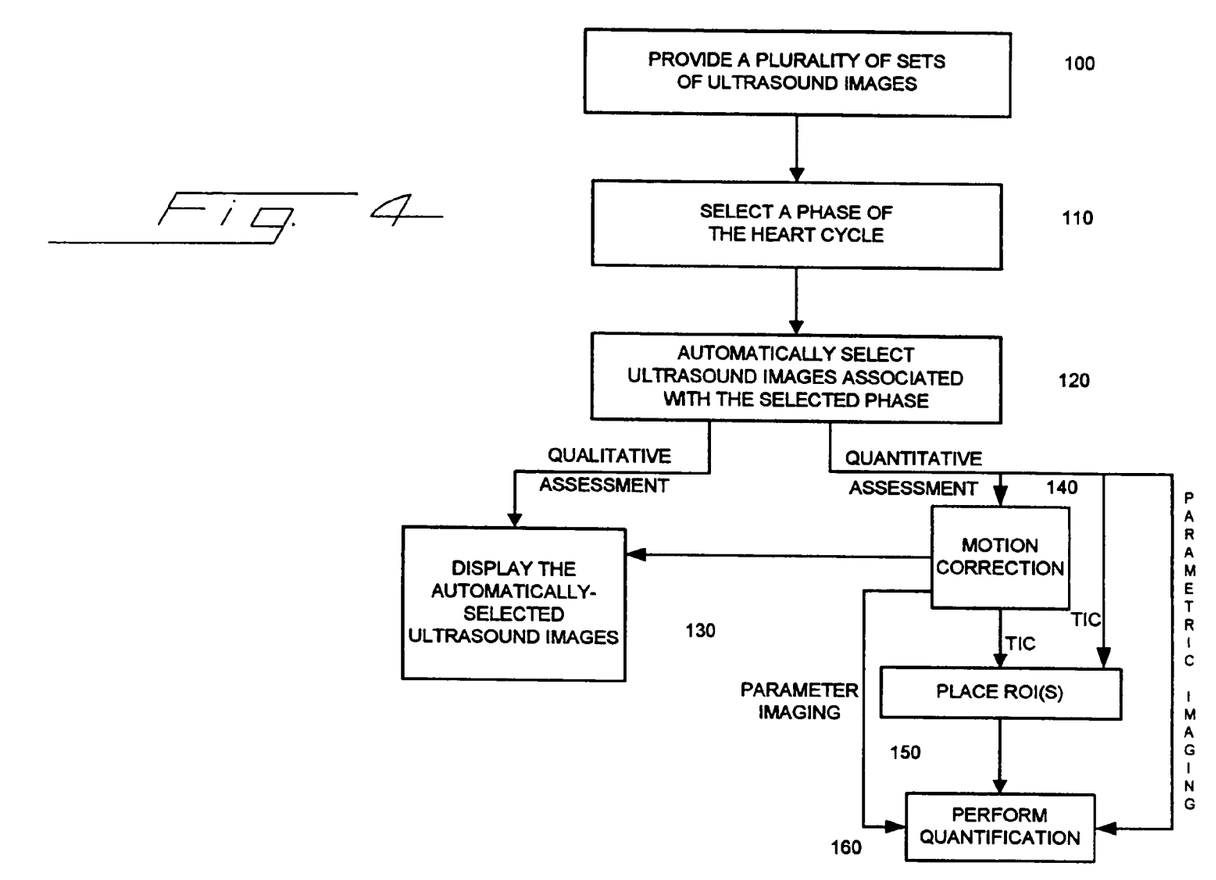
FIG. 4 is a flow chart of a method of an embodiment.

FIG. 4 is a flow chart of a method for phase selection for cardiac contrast assessment of an embodiment. As shown in FIG. 4, a plurality of sets of ultrasound images associated with a respective plurality of heart cycles is provided (act 100). Next, a phase of the heart cycle is selected (act 110), and ultrasound images associated with the selected phase are automatically selected (act 120). Next, qualitative and/or quantitative assessment is performed. With qualitative assessment, the automatically-selected ultrasound images are displayed for user assessment (act 130). With quantification assessment involving time intensity curves, one or more regions of interest are placed on an ultrasound image associated with the selected phase (act 150), and quantification analysis is performed (act 160). As shown in FIG. 4, with parametric imaging, no regions of interest are necessary (since quantification is done on each pixel).

Motion correction (act 140) can be used with either qualitative or quantitative assessment. It is important to note that while FIG. 4 shows a method with multiple acts, each of these acts can be used alone or in combination with one another. Additionally, these acts can be performed on an ultrasound system or an image review station (e.g., a dedicated workstation or a personal computer with a processor, display device, and user interface). These acts will now be discussed.

Providing a Plurality of Sets of Ultrasound Images

The first act of the method is to provide a plurality of sets of ultrasound images associated with a respective plurality of heart cycles (act 100). These images can be stored, for example, in a storage device in an ultrasound system or image review station, on removable media (e.g., a magneto-optical disc), or in a network location accessible by the ultrasound system or image review station.

With some of the embodiments below, it is preferred that the stored images be acquired using "real-time imaging." As used herein, the term "real-time imaging" refers to acquiring ultrasound images with a sufficiently high frame rate such that enough ultrasound images are acquired to allow the selection of an image associated with a desired phase of the heart cycle. "Real-time images" refers to images acquired during "real-time imaging." "Real-time imaging" is different from gated imaging, in which a portion of the heart cycle, such as an R-wave, triggers the acquisition of a single ultrasound image per heart cycle. "Gated images" refer to images acquired using gated imaging. Without intending to set a lower limit to the definition of "real-time imaging," an example of real-time imaging is acquiring ultrasound images at a frame rate of more than 15 frames per second. It should be noted that, as used herein, the term "real time" does not indicate when images are displayed with respect to a time of acquisition. Accordingly, images played from a stored clip can be "real time" images even though they are being displayed at a time after acquisition.

Selecting a Phase of the Heart Cycle

Figure 5:
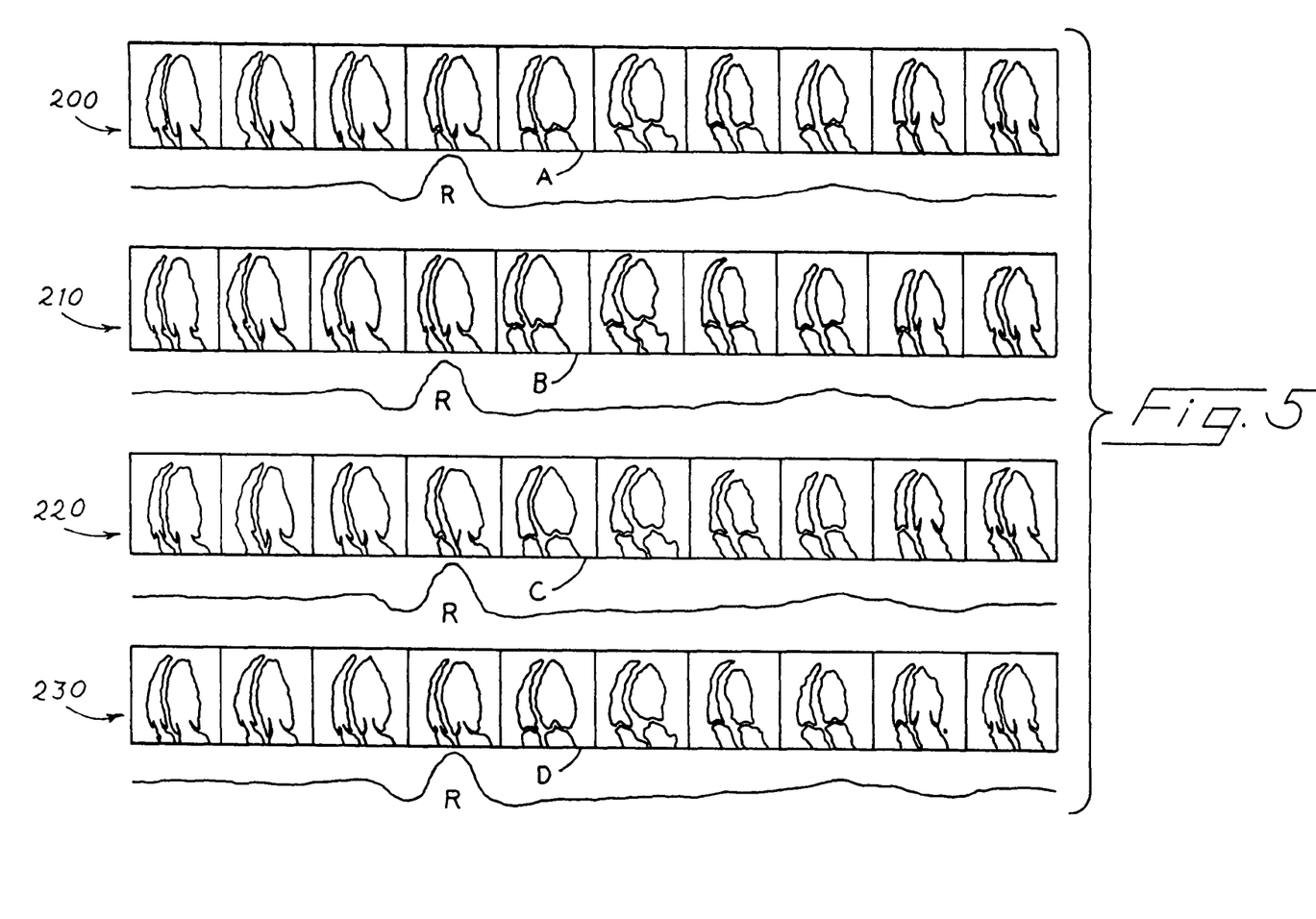
FIG. 5 illustrates a plurality of sets of ultrasound images of an embodiment.

Next, a phase of the heart cycle is selected (act 110). This act can be performed manually or automatically. FIG. 5 will be used to illustrate the manual operation. FIG. 5 shows a display of four sets 200, 210, 220, 230 of ultrasound images of an apical four-chamber view of the heart over four heart cycles. Each of the displayed images is associated with a particular phase of the heart cycle, and selection one of the displayed images selects a phase in the heart cycle. In operation, a user selects a displayed image to represent the cardiac phase that he is interested in based on the shape of the heart in the image or the state of the ECG signal associated with that image. For example, selection of image A selects a portion of the heart cycle that is X ms after the preceding R-wave.

In the automatic operation, a user can set a phase preference (e.g., X ms after the R-wave) that is stored in a storage device of the ultrasound system. In future examinations, the ultrasound system retrieves the stored user-preference to automatically select the phase rather than requiring the user to select a displayed image or take some other action to manually select the desired phase. A combination of the automatic and manual operations can be used. For example, the automatic operation can be used to initially select the phase, and, if the user is dissatisfied with this selection, the manual operation can be used.

Automatically Selecting Ultrasound Images Associated with the Selected Phase

For each of the plurality of sets of ultrasound images, an image associated with the selected phase of the heart cycle is automatically selected (act 120). This selection can be performed, for example, based on a time interval from a part of the heart cycle, such as the R-wave, or from image information. Each of these techniques will now be described.

Cardiac ultrasound machines provide a subsystem that measures physiological signals (such as the ECG signal) and present the information along with the ultrasound images as a reference, as shown in FIG. 5. The ultrasound system typically detects when the R-wave occurs in each heartbeat. The times for each R-wave can be stored along with the times of acquisition of each of the contrast images. The difference between the timestamp for each image and the time of the previous R-wave produces an interval that is analogous to the cardiac phase. Cardiac phase can be defined in a number of ways. The simplest method is to define only two phases of the heart—systole and diastole. This is similar to dividing a sinusoid into a negative phase and a positive phase. Sinusoidal phase can be more specifically defined using a phase angle, and, in a similar fashion, the phase of the cardiac cycle can be divided more finely. Although the phase angle does not fit for the cardiac cycle as it does for sinusoids, the phase can be defined as changing continuously during a cycle where the heart is in the same state during the same phase in all cycles. Irregularities can be considered as variations in the rate of phase change during a heartbeat or between heartbeats.

Figure 6:
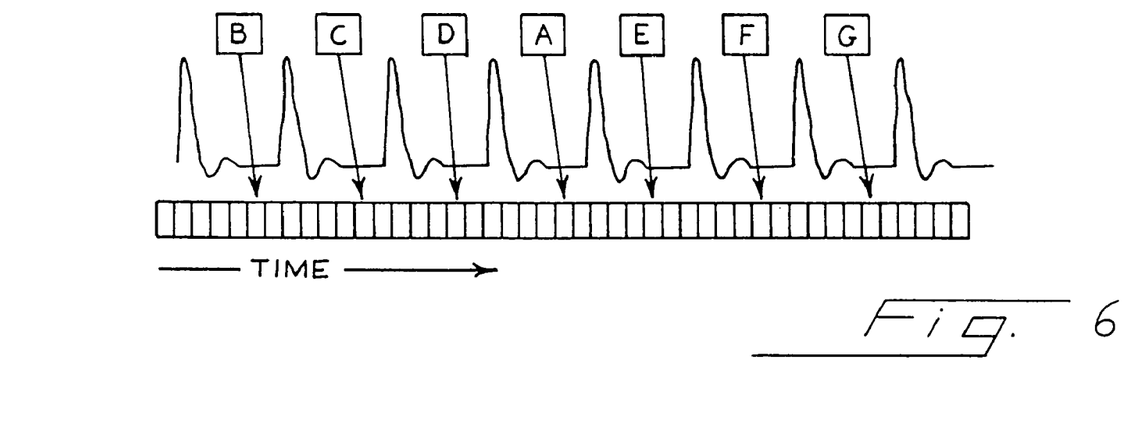
FIG. 6 is a timeline showing an ECG trace and times when image frames of an embodiment were acquired.

In operation, the time interval between a reference phase (e.g., a preceding R-wave) and the selected phase is determined. That time interval is then compared with the time interval between the reference phase and the phase associated with each image in a set of images from a heart cycle. An image in each cardiac cycle can be selected that has an interval from the preceding R-wave that most closely matches the interval for the image associated with the selected phased. With reference to FIG. 6, a timeline 300 shows an ECG trace and the times when image frames were acquired. Each rectangle indicates the time for one ultrasound frame. When a user selects image A, the ultrasound system automatically identifies frames B, C, D, E, F, and G as having a similar phase as A based on the ECG signal characteristics, such as the time interval from the preceding R-wave or some other characteristic of the ECG signal. In this way, the ECG information is used to sample an image clip at a rate of one frame per heartbeat at the selected phase to retain only images A-G for subsequent analysis.

If the imaging frame rate is irregular (possibly due to contrast destruction), there may not be an image that was acquired with a similar interval. In this case, the system preferably identifies that the match is poor and does not provide any images for some of the cardiac cycles. For example, a poor match can be defined as when the best match differs by more than 100 ms. Further, the above method relies on each cardiac cycle being identical. When there are irregularities, the interval between an image and the preceding R-wave may not give a good indication of the phase of the heart in that image. The interval to the succeeding R-wave can also be used to identify the cardiac phase in an image in question, although it should be acknowledged that the length of diastole varies to a much greater extent than does the length of systole. Other characteristics of the ECG signal can also be used to get a better estimate of the phase of a particular image. For example, the T-wave can be identified in order to better identify end-systole. This time can be used as another reference when determining the phase of a particular frame.

Instead of using ECG information, an image can be automatically selected based on one or more visual characteristics of an image, such as the shape of the heart and/or the state of the valves. In this way, visual characteristics are used to identify a phase in the heart cycle. In operation, an image from a set of images associated with a heart cycle is selected. This image can be manually selected by a user or automatically selected by identifying which image from the set is associated with a phase in a stored user-preference. Then, at least one visual characteristic from the selected image is compared to at least one visual characteristic of the ultrasound images from the other sets. The images that most-closely match (or match using some other criteria) would be automatically selected. With reference again to the illustration in FIG. 5, if the user selects image A, the ultrasound system would compare image characteristics such as position of the valve leaflets and/or the shape of the myocardium in image A with corresponding visual characteristics in other images in the clip to select the images that match most closely. In this example, A closely matches images B, C, and D, so images A, B, C, and D are used for subsequent analysis. (Alternatively, only the automatically-selected images (images B, C, and D) can be used for subsequent analysis and/or display.)

In the above discussion, only one frame per cardiac cycle was selected for analysis. In some cases, however, the heart does not change significantly over portions of the heart cycle.

For example, in diastole, there are periods where the heart is comparatively still. Several neighboring images from these quiet periods can be used in quantification (to provide more data points) without the complication of heart motion. To do this based on the time interval from the previous R-wave, the system would identify all the images that had intervals within some tolerance range of the interval for the user-selected image. Because the speed of the heart changes dramatically during the heart cycle, this tolerance range preferably varies based on the interval (e.g., longer for intervals within diastole and shorter for intervals within systole).

Qualitative Assessment

During qualitative assessment, the ultrasound images associated with the desired phase are displayed (act 130). By visually observing the images, the user can detect visible changes caused by contrast agent to make a diagnosis.

Quantitative Assessment

As described above, quantitative assessment (or analysis) refers to time intensity curve analysis, parametric imaging, displaying results of calculations, or any other contrast enhancement assessment technique (now existing or later developed) other than pure qualitative analysis. Quantitative assessment often relies on the placement of at least one region of interest. Although the region(s) of interest can be placed on an image before or after the automatic selection of images described above, placing the ROI(s) on an automatically-selected image allows a user to rapidly scroll through an image clip to check ROI placement in all the relevant images because the data set has been reduced to images at a particular cardiac phase. After the ROI(s) have been placed, quantification can be performed. For example, time intensity curves can be drawn for each phase of interest in the cardiac cycle. In one presently preferred embodiment, at least one region of interest used in quantification is user-defined and comprises more than nine pixels but covers less than the entire imaged tissue (e.g., the entire myocardium). As used herein, the term "pixel" refers to any one of the small discrete basic elements from which an image is composed.

Motion Correction

By selecting images from the same phase of the cardiac cycle, contractile cardiac motion is removed before further analysis. Contractile motion makes up a large part of the motion of the heart, but patient breathing and inadvertent probe movement can also cause motion of the heart in an ultrasound image. Preferably, this motion is also tracked in order to effectively quantify changes in the ultrasound signal received from the tissue. Many techniques have been developed to automatically determine the motion between pairs of images. While these techniques have been used, motion correction in a real-time image clip can be very difficult because of contractile cardiac motion. The phase selection techniques described above simplify motion correction because they allow motion tracking to be performed on a reduced set of images. By first identifying the phase to align, motion correction processing time can be reduced by a factor of 10-30 due to the reduction in the number of frames processed.

The motion between pairs of images can be used to change the location of the ROI's so that each ROI always encompasses the same tissue. Alternatively, after the motion has been determined, the images can be registered together so that the motion between the images is removed. Simple registration can allow the entire image to move as a unit to remove bulk motion. More complicated techniques register different parts of the image independently and stretch or shrink the intervening image in order to accommodate relative movement in an image.

The most successful motion detection techniques use correlation-based algorithms such as minimizing the sum of absolute differences (SAD). The SAD technique is a good choice because it is well-suited for rapid calculation. Using this technique, the absolute difference is calculated between each point in the original image and points in the subsequent image corresponding to each of many potential motions. The best estimate of the actual motion is chosen as the movement of the second image that produces the minimum of the sum of the absolute differences. When ROI's are tracked to eliminate motion, the SAD is preferably calculated between each ROI in the original image and possible motions of that ROI in the subsequent image. The minimum of the SAD for each ROI will provide an estimate of the position of each ROI in the subsequent image. When simple, bulk-movement registration is used, the SAD is preferably calculated for a large region in the center of the image. This will estimate the motion of the most important part of the image in order to eliminate that motion through registration. When more complicated registration techniques are used that accommodate relative movement in the image, the SAD is preferably calculated for many regions throughout the image. The movement of each of these regions can then be estimated based on the minimum of these SAD calculations and error checking. In this technique, more weight is preferably placed on the displacement estimates from some regions when calculating the displacement field for the image.

There are several alternatives that can be used with these embodiments. For example, while the embodiments described above have been illustrated using contrast-enhanced ultrasound images, these techniques can also be used with ultrasound images that are free of contrast agent. Further, as noted above, these embodiments can be used with real-time or gated images. For example, motion correction can be performed on gated images or images manually selected by a user from a real-time image clip instead of automatically-selected images. Further, motion correction can take place before or after region of interest placement and can be used in conjunction with either qualitative or quantitative assessment. Finally, as noted above, each of the embodiments described herein can be used alone or in combination with one another.

It is intended that the foregoing detailed description be understood as an illustration of selected forms that the invention can take and not as a definition of the invention. It is only the following claims, including all equivalents, that are intended to define the scope of this invention.

What is claimed is:

1. A method for automatically selecting ultrasound images associated with a phase of a heart cycle, the method comprising:

performing each of the following with a medical diagnostic ultrasound imaging system:

(a) storing a plurality of sets of ultrasound images, each of the plurality of sets comprising a plurality of ultrasound images, each of the plurality of ultrasound images associated with a different phase of heart cycle, wherein each ultrasound image is characterized by a time interval between an acquisition time of the ultrasound image and a reference phase in the heart cycle;

(b) retrieving a stored user-preference of a phase of the heart cycle, the user-preference being stored for selection of ultrasound images, wherein the user-preference is stored in the medical diagnostic ultrasound imaging system prior to acquisition of the plurality of sets of ultrasound images and, wherein the phase specified in the stored user preference is characterized by a time interval between the phase specified in the stored user preference and the reference phase;

(c) determining a tolerance range about the phase of the heart cycle, the tolerance range having a temporal width that is based on the time interval between the phase specified in the stored user preference and the reference phase;

(d) automatically selecting a plurality of ultrasound images from each heart cycle that are characterized by a time interval that is within the tolerance range; and (e) displaying the automatically-selected plurality of ultrasound images.

2. The method of claim 1, wherein the automatically-selected plurality of ultrasound images are from the diastole portion of the heart cycle.

3. The method of claim 1, wherein the tolerance range varies with the heart cycle.

4. The method of claim 3, wherein the tolerance range is greater for diastole than it is for systole.

5. The method of claim 1, wherein the reference phase comprises a preceding R-wave.

6. The method of claim 1, wherein the reference phase comprises a succeeding R-wave.

7. The method of claim 1, wherein the reference phase comprises a T-wave.

8. The method of claim 1 further comprising:
(f) motion correcting the automatically-selected plurality of ultrasound images.

9. The method of claim 1 further comprising:
(f) performing a quantification analysis on the automatically-selected plurality of ultrasound images.

10. The method of claim 1 further comprising:
(f) generating a set of time intensity curves using the automatically-selected plurality of ultrasound images.

11. The method of claim 1, wherein the ultrasound images comprise real-time images.

12. The method of claim 1, wherein the ultrasound images comprise contrast-enhanced ultrasound images.

13. The method of claim 1 further comprising placing at least one region of interest on an automatically-selected ultrasound image.

14. A method for automatically selecting ultrasound images associated with a phase of a heart cycle, the method comprising:
performing each of the following with a medical diagnostic ultrasound imaging system:
(a) storing a plurality of sets of ultrasound images, each of the plurality of sets comprising a plurality of ultrasound images, each of the plurality of ultrasound images associated with a different phase of heart cycle, wherein each ultrasound image is characterized by a time interval between an acquisition time of the ultrasound image and a reference phase in the heart cycle;

(b) receiving a user selection of one of a plurality of displayed ultrasound images, each of the displayed ultrasound images being associated with a respective phase of the heart cycle, wherein the phase associated with the user-selected image is characterized by a time interval between the phase associated with the user-selected image and the reference phase;

(c) determining a tolerance range about the phase of the heart cycle, the tolerance range having a temporal width that is based on the time interval between the phase specified in the stored user preference and the reference phase;

(d) automatically selecting a plurality of ultrasound images from each heart cycle that are characterized by a time interval that is within a tolerance range of the time interval between the phase associated with the user-selected image and the reference phase; and (e) displaying the automatically-selected plurality of ultrasound images.

15. The method of claim 14, wherein the automatically-selected plurality of ultrasound images are from the diastole portion of the heart cycle.

16. The method of claim 14, wherein the tolerance range varies with the heart cycle.

17. The method of claim 16, wherein the tolerance range is greater for diastole than it is for systole.

18. The method of claim 14, wherein the reference phase comprises a preceding R-wave.

19. The method of claim 14, wherein the reference phase comprises a succeeding R-wave.

20. The method of claim 14, wherein the reference phase comprises a T-wave.

21. The method of claim 14 further comprising:
(f) motion correcting the automatically-selected plurality of ultrasound images.

22. The method of claim 14 further comprising:
(f) performing a quantification analysis on the automatically-selected plurality of ultrasound images.

23. The method of claim 14 further comprising:
(f) generating a set of time intensity curves using the automatically-selected plurality of ultrasound images.

24. The method of claim 14, wherein the ultrasound images comprise real-time images.

25. The method of claim 14, wherein the ultrasound images comprise contrast-enhanced ultrasound images.

26. The method of claim 14 further comprising placing at least one region of interest on an automatically-selected ultrasound image.

* * * * *